United States Patent [19]
von Gise

[11] Patent Number: 4,543,236
[45] Date of Patent: Sep. 24, 1985

[54] INCUBATING APPARATUS FOR SELECTIVE AND EXACT TREATMENT OF HISTOLOGICAL PREPARATIONS

[76] Inventor: Hardo F. von Gise, Schwärzlocher Strasse 110, 7400 Tübingen, Fed. Rep. of Germany

[21] Appl. No.: 357,555

[22] Filed: Mar. 12, 1982

Related U.S. Application Data

[63] Continuation of Ser. No. 135,619, Mar. 31, 1980, abandoned.

[30] Foreign Application Priority Data

Apr. 14, 1979 [DE] Fed. Rep. of Germany ....... 2915248

[51] Int. Cl.[4] .............................................. G01N 1/30
[52] U.S. Cl. ...................................... 422/50; 422/99; 422/103; 134/95; 134/100; 134/61; 435/284; 435/285; 435/310; 118/50; 118/421; 118/429; 118/702
[58] Field of Search ................... 422/67, 99, 104, 102, 422/275, 50, 103; 435/291, 285, 284, 310; 134/99, 103, 95, 98, 100, 101, 61; 137/255, 266; 118/702, 50, 421, 429; 427/4

[56] References Cited

U.S. PATENT DOCUMENTS

| | | | |
|---|---|---|---|
| 3,227,130 | 1/1966 | Weiskopf | 118/11 |
| 3,400,726 | 9/1968 | De Bernard Du Grail | 134/95 |
| 3,664,354 | 5/1972 | Minbiole, Jr. et al. | 134/61 |
| 3,825,410 | 7/1974 | Bagshawe | 422/66 |
| 4,141,312 | 2/1979 | Lauder et al. | 422/67 |
| 4,358,470 | 11/1982 | Rasmussen | 427/4 |
| 4,398,382 | 8/1983 | Suovaniemi | 422/99 |

Primary Examiner—William F. Smith
Attorney, Agent, or Firm—Michael J. Striker

[57] ABSTRACT

An incubating apparatus allowing selective and exact treatment of histological preparations with reagents. The incubating apparatus consists of an incubating unit holding the preparations to be treated, which is supplied with reagents from a reagents storage through a supply section. Herein, a computerized control section will implement automatic control, as per program, of all components, particularly valves and pumps, and of the supply section, so that automatic sequencing of the treatment in the incubating apparatus can be achieved.

4 Claims, 7 Drawing Figures

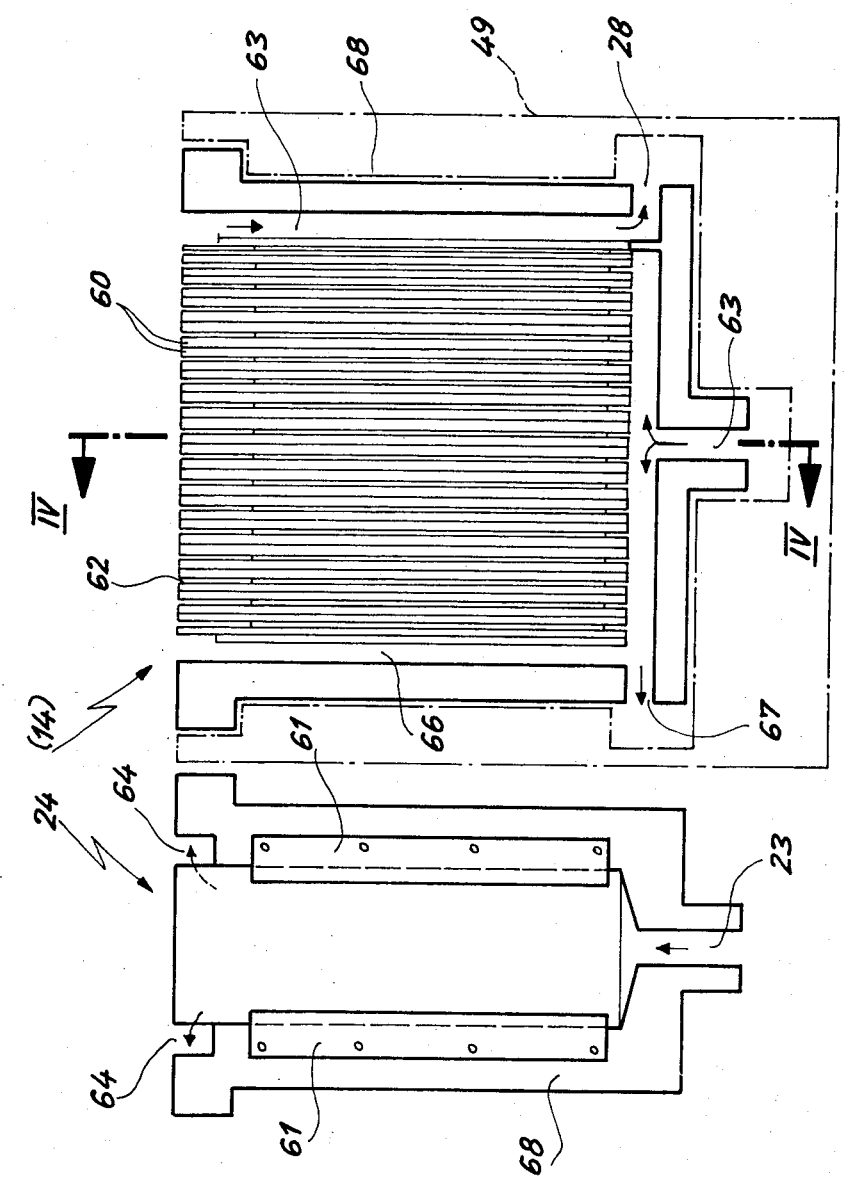

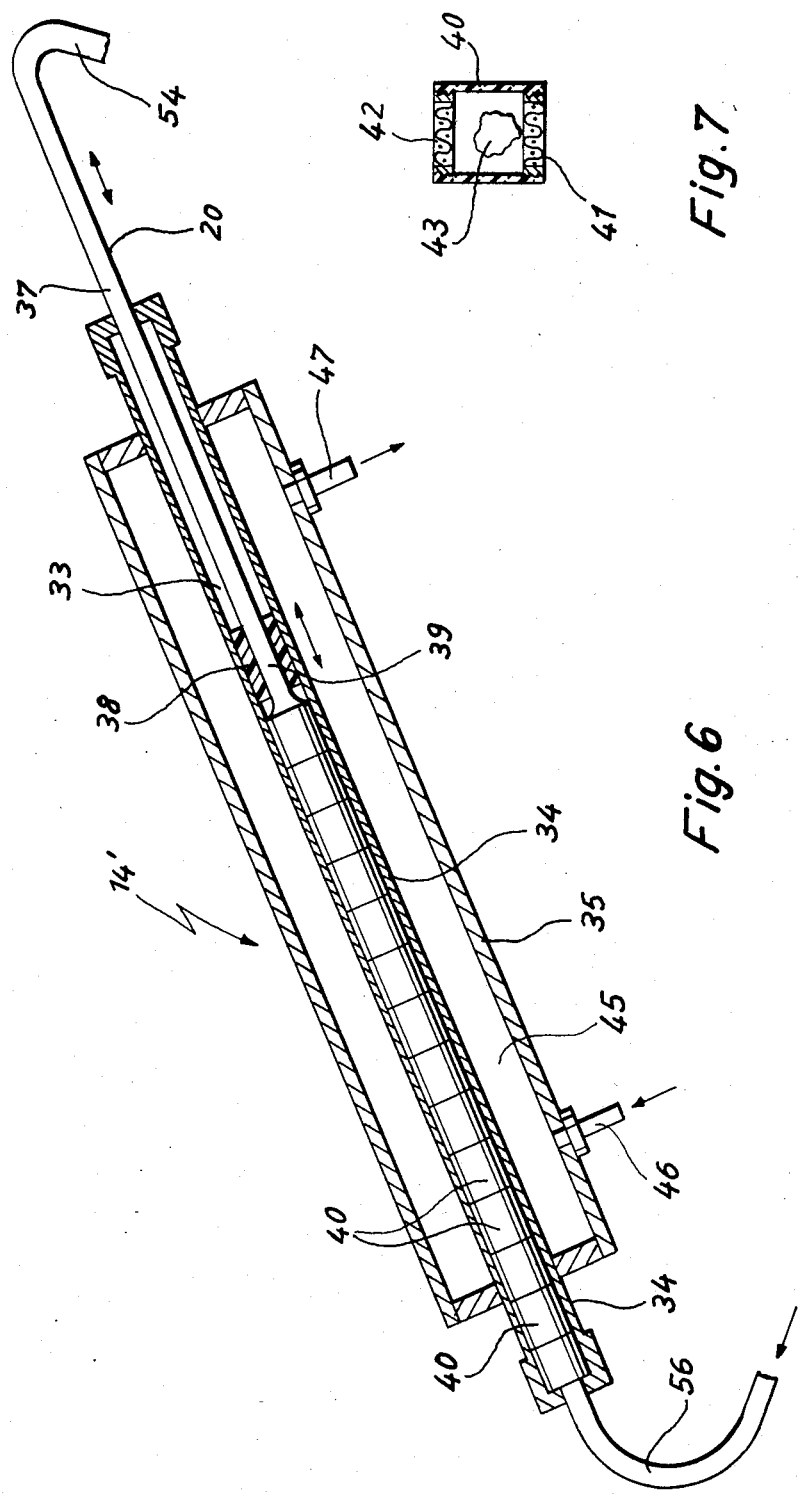

INCUBATING APPARATUS FOR SELECTIVE AND EXACT TREATMENT OF HISTOLOGICAL PREPARATIONS

This is a continuation of application Ser. No. 135,691, filed Mar. 31, 1980, now abandoned.

BACKGROUND OF THE INVENTION

The invention relates to an incubating apparatus for the selective and exact treatment of histological preparations.

Treatment of histological preparations has hitherto been made mainly by hand. Apparatus available on the market for a partial mechanization of histological methods can be applied only for some individual processes. There has not been, hitherto, a variable apparatus universally suitable and applicable for all methods of incubating and imbedding of biological preparations. The various histological incubating techniques as implemented, require not only a large labor expenditure but also extreme care, so that methods of immuno-histology and histo-chemistry cannot be performed by unskilled staff or such as has been trained on the job. Maintenance of uniform temperatures are of uniform periods of activity can be made herein only with difficulty, so that reproduceable results cannot be insured.

Such deficiencies may have grave consequences, since the incubation of histological preparations may be of importance for the results of immuno-histological or histo-chemical examinations or electron microscopy, and thus decisive for a diagnosis. This applies in particular to renal diagnostics or for the immuno-histological or histo-chemical classification of tumors.

The invention has as its objective the creation of an incubating apparatus allowing manifold and also automatic, treatment of histological preparations of the most various types.

SUMMARY OF THE INVENTION

The objective, as set, is attained as per invention by an incubating apparatus characterized by an incubating unit for the holding of a plurality of preparations to be treated, which is connected to a reagent storage through a supply section effecting supply and draining of reagents. For automatic operation of the incubating apparatus, the supply section may advantageously be coupled with a control section equipped with a computer. The preparations to be treated may be treated in various forms, for instance as prepared sections, or unsectioned tissue, wherein the incubating unit may be adapted to the respective type of specimen carrier. Reagents are to be understood as any type of material transportable through piping or hose lines, including materials such as plastics or paraffin wax serving imbedding of preparations for optical or electronic microscopy.

An incubating apparatus constructed as per invention will allow virtually the entire range of known histological incubating techniques, and subject these to an exact, programmable, automatic sequence. Not only the exact composition of the reagents, but exact reaction times and treatment temperatures will be insured herein, and also an economic use of the reagents which frequently are very expensive.

An incubating apparatus constructed as per invention will allow the performance, with great precision, of immuno-histological methods on paraffin sections, methods of quantitative histo-chemistry on histological section preparations, and also labor-intensive special dyeings which do not occur routinely.

By virtue of the adaptability or exchangeability of the incubating unit as noted before, the apparatus may also be used for the imbedding of preparations for electron microscopy. If the incubating apparatus is equipped with computer control, treatment methods of a difficult nature may be performed by unskilled staff or staff trained on the job.

The supply section is provided with valves and at least one pump arranged in the supply or drain passages for the reagents, electrically actuated from the control section. It will be of advantage if every reagent container of the reagent storage is connected by a separate inlet valve of the supply section to a common pump-equipped manifold line of the supply section, with the supply section suitably having a branch-off with a shut-off valve of the common manifold line for every holding chamber of the incubating unit. Every holding chamber of the incubating unit is connected over an adjustable valve of the supply section with a drain leading to a waste container, and the supply section may advantageously be provided with at least one additional vacuum pump which can be connected at the drain side of the incubating unit. This pump will also serve, intermittently or continually, for the evacuation of reagents or solvent vapors which must not be allowed to influence the work place. By the design of the supply section and the incubating unit as noted above, the incubating apparatus may be applied to many uses. Taking advantage of a corresponding construction of the supply section, and corresponding control of its valves and pumps, work may selectively be perfomed either in only one, or, simultaneously, in a plurality of holding chambers of the incubating unit. The supply section may easily be designed so that simultaneously work may be performed in a plurality of holding chambers of the incubating unit using different reagents. The supply section can also fulfill the requirement of draining different reagents into different waste containers. It will be of advantage when the supply lines, and the units of the supply section connected to these, can selectively be connected by additional valves to a container for flushing agents, so that using the delivery device, for instance a pump, or using the evacuating device for the supply section, all lines and units of the supply section can be cleaned with a flushing agent before being supplied with a different reagent.

Advantageously, the incubating apparatus of an embodiment as per invention may also be coupled with a thermostat section by the use of which, in connection with heating or cooling devices, it will be possible to hold the incubating unit and, in given instances also units of the reagents storage, at the respective temperature desired for reaction or storage. The holding chambers of the incubating unit will be arranged herein preferably in such a manner that they are at least in part enclosed by a peripheral housing, with the temperature of the latter being controlled by the thermostat section.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

DESCRIPTION OF THE PREFERRED EMBODIMENTS

Figure 1:
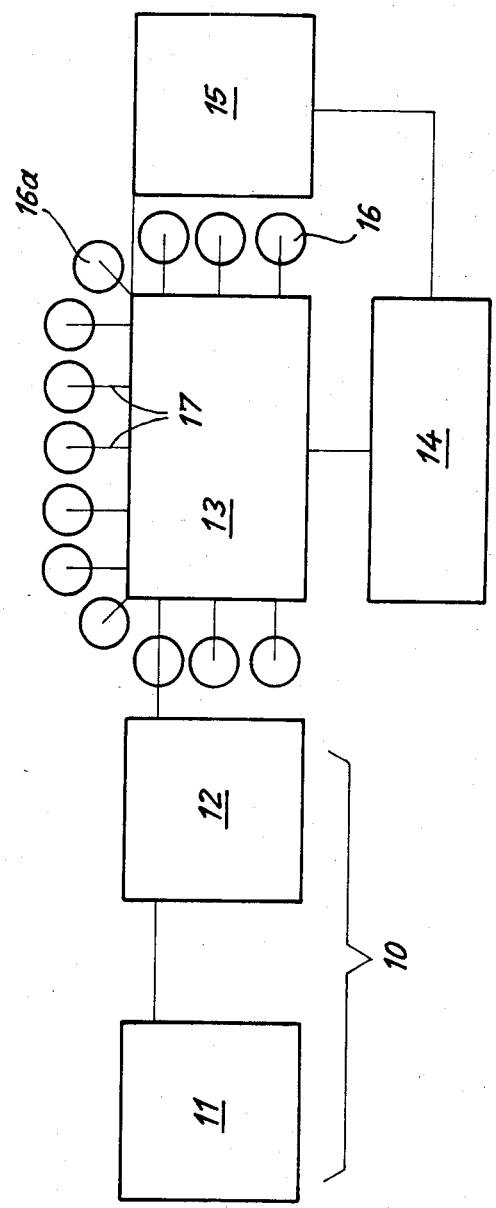
FIG. 1 a general diagram of the entire apparatus.

As per the general diagram of FIG. 1, the incubating apparatus is provided with a two-part control section 10, consisting of a desktop computer 11 and a subsequently arranged interface stage 12, a supply section 13, an incubating unit 14, a thermostat section 15 and a reagent storage 16. Several individual reagent containers 16a of the reagent storage 16 are shown symbolically with their connecting lines 17 leading to the supply section 13. Supply section 13 is provided with electrically actuated valves and pumps, and is controlled from the computer-equipped control section 10 in order to feed the incubating unit 14 with reagents. Temperature control of the supply section and the incubating unit is effected by means of the thermostat 15 whereby control of the supply section 13 may ensue depending upon the temperature in the incubating unit 14. All components of the incubating apparatus may be arranged or held on a common frame or in a common housing.

A commonly available desktop computer, programmable to a sufficient extent, may be used as the computer 11. The interface stage 12, which may be integrated into the supply section, is of such a design that it will convert the computer signals into suitable control signals for the individual units of the supply section 13, especially the valves and pumps.

The specific design of the control section 10 and of the thermostat stage 15 which also effects some control functions is not essential to the invention and will thus not be described in greater detail.

Figure 2:
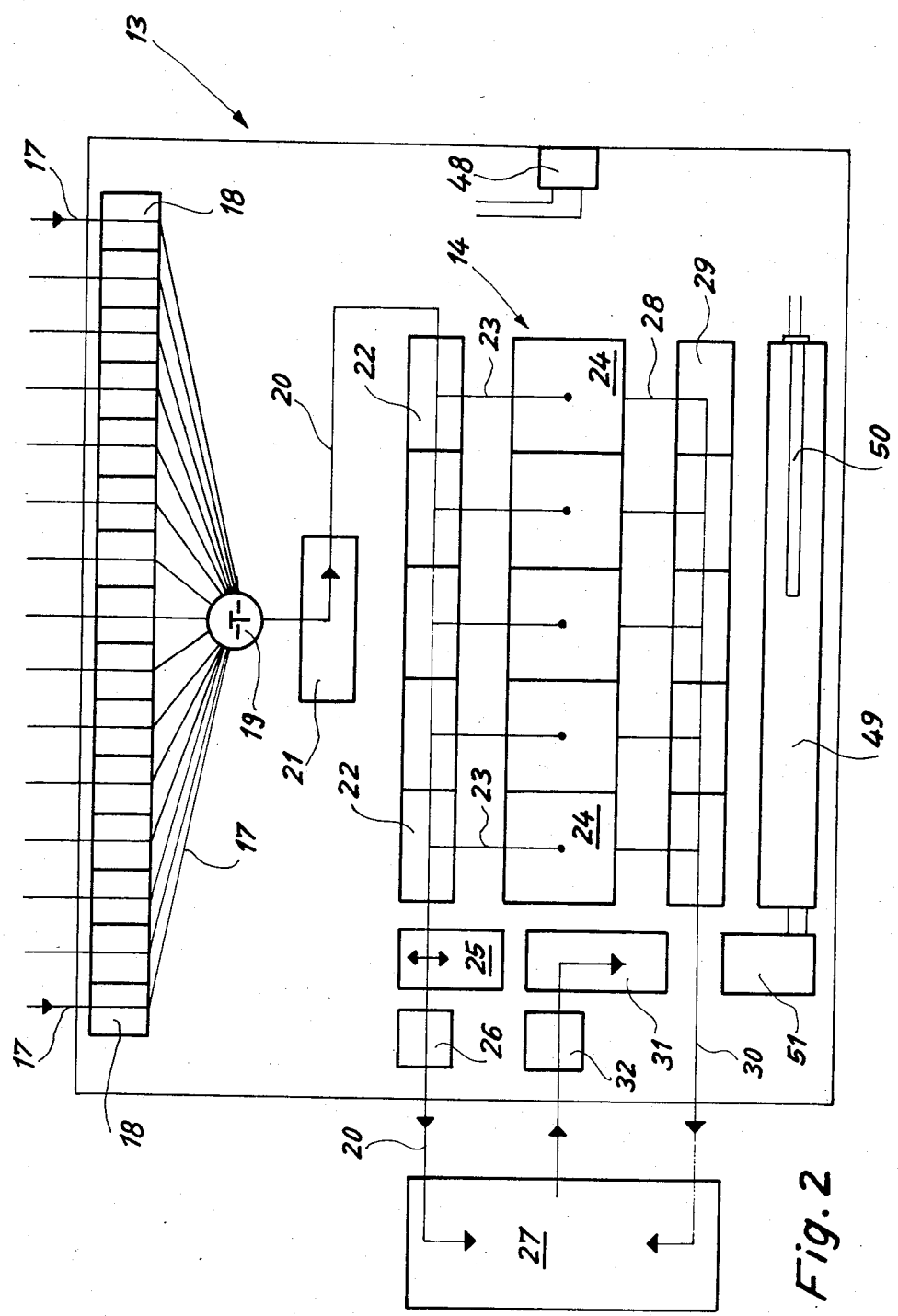
FIG. 2 a schematic of the function of the supply section and incubating section of a first embodiment of the incubating apparatus, FIG. 3 a schematic longitudinal section through a treatment chamber of the incubating unit of an embodiment as per FIG. 2, FIG. 4 a section along the line IV—IV in FIG. 3, FIG. 5 a scheme of the function of the supply section and the incubating section of a second embodiment of the incubating apparatus, FIG. 6 a central longitudinal section through a treatment chamber of the incubating unit as per the second embodiment, and FIG. 7 a section through a specimen carrier used in the treatment chamber as per FIG. 6.

FIG. 2 shows in a schematic view a first embodiment of the supply section 13 in connection with an incubating unit 14 serving for the treatment of prepared sections which are deposited on specimen carriers in the form of glass slides, which will be described in connection with FIGS. 3 and 4. The supply section 13 is provided with an adjustable shut-off valve 18 for every connecting line 17 coming from a reagent container 16a (FIG. 1). In the embodiment shown in FIG. 2, connecting lines are provided and correspondingly also fifteen adjustable shut-off valves 18. After the shut-off valves 18, all connecting lines 17 lead into a common central chamber 19 wherein check valves, not shown, are arranged at the end points of the connecting line 17 and wherein a mixture may already take place of several reagents that are simultaneously lead in. A supply manifold 20 with a supply pump 21 arranged in it, leads from the chamber 19 to the inlet side of the incubating unit 14 from which branch passages 23, controlled by shut-off valves 22, lead into the individual chambers 24 of the incubating unit 14. In the embodiment shown, the incubating unit 14 is provided with five individual chambers 24. Correspondingly, provision is also made for five branch passages 23 and five shut-off valves 22. The manifold line 20 then leads through a pulsing device 25 which serves to keep in continual motion the reagents in the manifold line 20 and also to circulate the preparations in the chamber, and then through a normally closed shut-off valve 26 to a waste container 27.

At the drain side of the incubating unit 14, a drain passage 28 will lead from every chamber 24 of this unit over a respective shut-off valve 29, into a common drain line 30 ending in the waste container 27.

FIG. 2 also shows a vacuum pump 31 which is connected over a valve 32 to the interior of the waste container 27. Draining of reagents or of flushing agent from the collector passages 20 and 30 into the waste container 27 can be effected by means of this vacuum pump. Additional reagents can be brought from the exterior into the supply section 13 through a connecting passage 48, which is just indicated, and can be introduced into the passage system from the former at a suitable location.

A pan is located below the incubating unit 14, with a heating rod 50 extending into it. Pan 49 is filled with a heat transfer medium moved by a circulation pump 51. This pan 49 shall symbolically represent the peripheral housing 49 indicated in FIG. 3 which serves for heating or cooling the chambers 24 of the incubating unit 14. It is understood that all components of the supply section as shown in FIG. 2, i.e. valves, pumps and heating devices can be actuated electrically or electronically and are connected with the control section 10 and/or the thermostat section 15 of the incubating apparatus by connecting lines which, for reasons of clarity, are not shown in FIG. 2.

FIGS. 3 and 4 show schematic sections through the incubating unit used in the embodiment as per FIG. 2. All five chambers 24 of this incubating unit 14 are designed to treat preparations arranged on specimen carriers 60 in the shape of flat plates. The glass specimen carriers 60 are arranged in pairs back to back, except those carriers located at the edge, and a small slot 62, for the passage of liquid reagents is provided between every pair of specimen carriers by means of spacer brackets 61.

The glass specimen carriers 60 are arranged vertically, so that also the narrow passage gaps 62 will run vertically. The reagent supply, i.e. the connection for the branch-off passage 23 is designed at the bottom of the incubating chamber 24. The reagents in the reagent chamber will ascend through the passage slots 62, or they are lifted by means of the vacuum pump 31 (FIG. 2), into an incubating unit 14 which is tightly closed by a cover. The upper opening of the chamber housing 68, made for instance from plastic and suspended into a heatable peripheral housing 49 indicated by dot-dash lines, is provided with encircling overflow channels 64 leading into an overflow passage 64 that ends at the connection, located near the bottom, of the drawn passage 28. A riser pipe 68 is furthermore arranged in the chamber housing 66 through which gas that has collected and reached the chamber 24 may be drained off. An additional drain opening 67 is provided in the bottom zone of the chamber housing 68. Gases will be evacuated by means of the vacuum pump 31.

Figure 5:
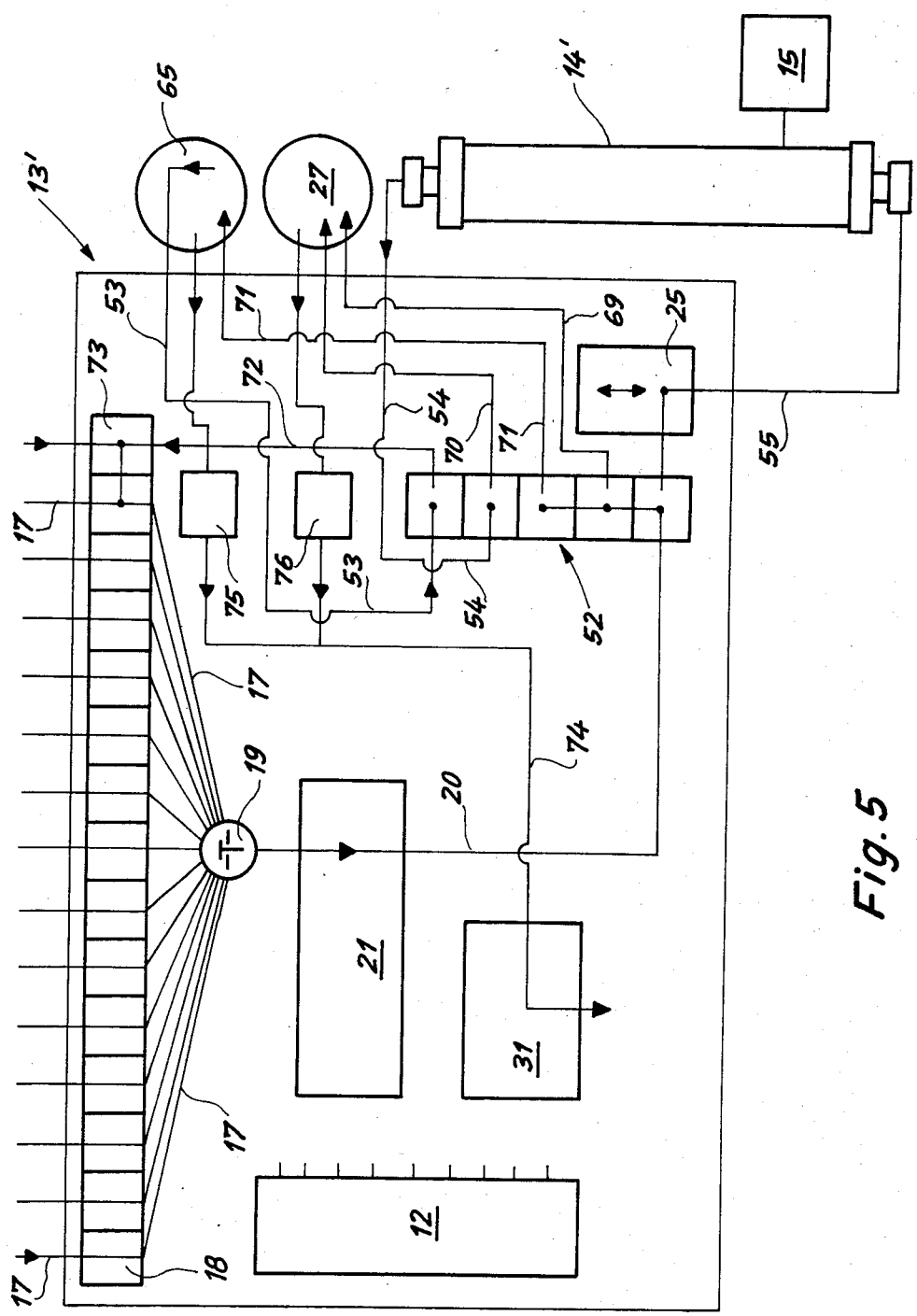

FIG. 5 shows the schematic of the functioning of the supply section 13' of a second embodiment of the incubating apparatus, provided with a different embodiment of the incubating unit 14'. Identical components as in embodiment as per FIG. 2 are denoted by identical reference numbers, and are not described anew. In the embodiment as per FIG. 5 the collector passage 20 provided with the supply pump 21 leads to the inlet of a changeover valve 52 having several positions. The valve is provided with additional inlets for a flushing supply line 53 coming from a flushing reservoir 65, and also for the drawn line 54 coming from the incubating unit 14'. At the exit side, the changeover valve 52 is connected to the supply line 55 leading to the incubating unit 14, to two drain lines 69 and 70 leading to the waste container 27, to a flushing return line 71 leading to the flushing reservoir 65 and to a flushing connection line 72. The supply line 55 to the incubating unit 14' is provided with a pulser 25 to generate motion of the liquid in the chamber. The flushing connection line 72 is selectively connectable by an additional inlet valve 73 with a section of one of the connecting lines 17 leading to the central chamber 19.

The vacuum pump 31 of the supply section 13' can be selectively connected via a suction line 74 and two shutoff valves 75 and 76, either with flushing reservoir 65 or waste container 27.

The thermostat section 15 covering the incubating unit 14' is also represented in FIG. 5, as is the interface stage 12 which in the embodiment is integrated into the supply section 13'. The control lines leading from this interface stage 12 to the individual electrically actuated valves and pumps of the supply section are again not shown here for reasons of clarity.

Depending upon the position of the multiple-stage changeover valve 52, which is computer controlled over the interface stage 12, reagents are supplied into the incubation unit 14' through the manifold line 20 and the connecting line 55, and drained into the waste container 27, or delivery can be made by the vacuum pump 31 of flushing agent from the flushing reservoir through the flushing connecting line 72 into the central chamber 19 and then through all passages of the supply section 13 as used, and finally into the waste container 27. On actuating the flushing circuit, the delivery pump may simultaneously be actuated. When repositioning the changeover valve 52, concomitant positioning of a part of the other valves will ensue, corresponding to the desired connections within the supply section 13'. FIG. 6 shows a schematic longitudinal section through a treatment chamber 33 of the incubating unit 14' used in the embodiment as per FIG. 5. This treatment chamber 32 may be provided singly, or together with additional automatic treatment chambers. The treatment chamber 33 is housed within a tube 34 concentrically arranged in an outer tube 35. A reagent supply line 56 is connected to one end of the tube. The hollow piston rod 37 of a piston 38 introduced into the tube 34 forming a seal, which has a central passage 39 communicating with the hollow piston rod 37, extends through the other tube end. Several specimen capsules 40 are arranged in the treatment chamber 33 formed by the tube 34, one of the first-named being shown individually in section in FIG. 7. The cylindrical specimen capsules 40 are provided with a mesh bottom 41 and a removable mesh cover 42, which may be secured on the specimen capsules 40 by a thread or bayonet-type lock. The specimen capsules 40 are so aligned in the tube 34 that the mesh cover 42 of one capsule 40 is contiguous to the mesh bottom 41 of the adjoining capsule. The specimen capsules 40 are kept in tight abutment by means of the piston 38. The reagents entering the tube 34 through the supply line 56 will then flow further through all specimen capsules 40 and through the opening 39 of the piston 38, and finally through the hollow piston rod 37 into the drain line 54 connected to the hollow piston rod 37. The ends of the outer tube 35 are closed. A heating or colling medium may be led over a supply line 46 and a drain line 47 through the annular space 45 between inner tube 34 and the outer tube 35.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

I claim:

1. Incubation apparatus for use in the processing of histological preparations, having reagent storage means including a plurality of reagent containers, said containers being connectable with incubating means for the holding of a plurality of preparations, said incubating means comprising at least one treatment chamber having an inlet and an outlet at different ends and being composed of tubing within which gas and liquid permeable specimen capsules are arranged in adjoining relationship and are in abutment by means of a hollow piston.

2. The incubation apparatus according to claim 1, wherein said specimen capsules have mesh bottoms and mesh covers and are arranged with their mesh sides being contiguous with the mesh bottom of the adjoining capsule.

3. The incubation apparatus according to claim 1, wherein said treatment chamber tubing is arranged concentrically in an outer tube or greater diameter, thereby forming an annular space between said tubing and said outer tube, through which a heating or cooling medium can flow.

4. The incubation apparatus according to claim 1, further comprising supply section means with programmable valves and pumps, said supply section means including a multiple-stage changeover valve having an entry side and a discharge side, having on its entry side a connection for and being connected with a manifold line for said reagent, a connection for and being connected with a flushing agent supply line leading from a flushing agent reservoir, and a connection for and being connected with a drain line from said incubating means, and on its discharge side connections for and being connected with a supply line to said incubating means, a flushing agent return line to said flushing agent reservoir, a flushing agent connection line leading into said supply section means and a drain line leading into said waste container means.

* * * * *